United States Patent [19]

Hassan et al.

[11] Patent Number: 5,851,514
[45] Date of Patent: Dec. 22, 1998

[54] STABLE AQUEOUS ABRASIVE PEROXIDE TOOTH WHITENING DENTIFRICE

[75] Inventors: Mahmoud Hassan, Piscataway; Nagaraj Dixit, Plainsboro; Michael Prencipe, Princeton Jct.; David B. VIscio, Monmouth Junction; Salim A. Nathoo, Piscataway, all of N.J.

[73] Assignee: Colgate Palmolive Company, New York, N.Y.

[21] Appl. No.: 692,841

[22] Filed: Aug. 2, 1996

Related U.S. Application Data

[60] Provisional application No. 60/004,336 Sep. 26, 1995.
[51] Int. Cl.⁶ .................. A61K 7/16; A61K 7/20
[52] U.S. Cl. .................................. 424/53; 424/49
[58] Field of Search ........................... 424/49–58

[56] References Cited

U.S. PATENT DOCUMENTS

| | | | |
|---|---|---|---|
| 3,864,271 | 2/1975 | Stalter | 259/99 |
| 4,297,298 | 10/1981 | Crommelynck et al. | 260/502 |
| 4,788,052 | 11/1988 | Ng et al. | 424/53 |
| 4,839,156 | 6/1989 | Ng et al. | 424/53 |
| 4,839,157 | 6/1989 | Ng et al. | 424/53 |
| 4,895,721 | 1/1990 | Drucker | 424/53 |
| 4,981,662 | 1/1991 | Dougherty | 423/272 |
| 5,059,417 | 10/1991 | Williams et al. | 424/53 |
| 5,130,053 | 7/1992 | Feasey et al. | 252/400 |
| 5,171,564 | 12/1992 | Nathoo et al. | 424/53 |
| 5,217,710 | 6/1993 | Williams et al. | 424/53 |
| 5,256,402 | 10/1993 | Prencide et al. | 424/53 |
| 5,279,816 | 1/1994 | Church et al. | 424/53 |
| 5,437,858 | 8/1995 | Hungerbach et al. | 424/53 |
| 5,597,554 | 1/1997 | Wagner | 424/53 |

FOREIGN PATENT DOCUMENTS

| | | | |
|---|---|---|---|
| 0288420 | 10/1988 | European Pat. Off. | A61K 7/20 |
| 0325267 | 7/1989 | European Pat. Off. | A61K 7/20 |
| 0535816 | 4/1993 | European Pat. Off. | A61K 7/16 |
| 0545594 | 6/1993 | European Pat. Off. | A61K 7/20 |

*Primary Examiner*—Shep K. Rose
*Attorney, Agent, or Firm*—Paul Shapiro

[57] ABSTRACT

An aqueous abrasive whitening composition containing a peroxide whitening compound which is chemically and physically stable and exhibits heightened and rapid whitening of teeth and stain removal which comprises a combination of water, abrasive and peroxide compounds, a humectant containing a polyethylene glycol, a polyoxyethylene-polyoxypropylene block copolymer, a metal ion complexing agent and an antioxidant, the pH of the composition being in the range of about 5.8 to about 7.2.

12 Claims, No Drawings

STABLE AQUEOUS ABRASIVE PEROXIDE TOOTH WHITENING DENTIFRICE

BACKGROUND OF THE INVENTION

1. Field of the Invention

This invention relates generally to peroxide containing preparations for whitening human teeth, and more particularly, to a stable peroxide dentifrice composition which when applied onto the surface of teeth acts to both whiten and remove stain from teeth.

2. The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a film over the teeth. These staining and discoloring substances can then permeate the enamel layer. This problem occurs gradually over many years, but imparts a noticeable discoloration of the enamel of one's teeth.

There are available in the marketplace non-abrasive gel compositions for home use which contain 1–3% by weight concentrations of hydrogen peroxide or urea peroxide and when brushed on the teeth effect whitening and removal of stains.

A drawback to the use of these peroxide based whitening gels is the tendency of the peroxide component to decompose within a relatively short period of time following manufacture with concomitant loss of all or a substantial amount of the available oxygen thereby limiting the efficacy of these products as teeth whitening compositions. Peroxy compounds such as hydrogen peroxide are notoriously unstable with respect to maintenance of peroxide level and have been found to be difficult to formulate into aqueous gels or pastes which will have an adequate shelf-life and yet will readily liberate oxygen when applied to teeth. Therefore, the prior art, for example U.S. Pat. Nos. 4,988,450 and 3,657,413, in formulating oxygen liberating compositions for the whitening of teeth, utilize anhydrous powders or water-free pastes or gels which must be protected against chemical interaction. A drawback to the use of such anhydrous products is that, due to the absence of water, application of the product tends to desiccate oral tissue which leads to irritation and tissue damage.

Dentifrice whitening products formulated with peroxy compounds normally do not contain abrasive polishing agents as such materials activate the rapid decomposition of the peroxy compounds whereby the oxygen whitening agent is prematurely released. The gas evolution is especially undesirable as such gas evolution can cause swelling and/or bursting of tubes containing the dentifrice product. Capped tubes filled with dentifrice products containing peroxy compounds and silica abrasives have been known to explode within one day after filling. When alumina abrasives are substituted for silica, the filled product is pocketed with gas bubbles within days of filling.

A drawback to the use of whitening products which are formulated without abrasives is that, in addition to the stability problem, the products are not effective in stain removal. Thus the abrasive or polishing agent incorporated in a dentifrice acts to debride and physically scrub the external surface of teeth. This scrubbing action removes filmy bacterial and plaque layers as well as some of the stains and discoloring pigments that are found on teeth that cause the undesired discoloration. These abrasive agents also microabrade the tooth so as to polish the teeth to give the enamel a more lustrous appearance and a higher optical sheen. This micro abrasion action enhances the scrubbed teeth's ability to reflect white light and thereby appear brighter.

Illustrative of non-abrasive oral compositions containing peroxide compounds include U.S. Pat. Nos. 4,980,152; 4,839,156; 4,522,805 and 4,567,036.

U.S. Pat. No. 4,980,152 discloses a non-abrasive aqueous oral gel composition comprising about 0.5 to about 50% by weight urea peroxide and 0.01 to 2% by weight of a fluoride providing compound. The composition further includes a thickening agent such as carboxypolymethylene, a non-ionic surfactant, alkali soluble cellulose ethers as thickening agents, potassium phosphate as a buffering agent and glycerin as a carrier and flavoring and sweetening agents.

U.S. Pat. No. 4,839,156 discloses an aqueous dental gel containing 18–25% by weight of a polyoxyethylene polypropylene block copolymer gelling agent, hydrogen peroxide, flavor, sweetening agent and a non-ionic surfactant as the essential ingredients.

U.S. Pat. Nos. 4,522,805 and 4,567,036 disclose a stable toothpaste to aid in controlling periodontal disease, containing an oxidizing agent such as urea peroxide in a carrier comprising an anionic detergent, sorbitol and glycerin humectants and a thickening agent such as gum tragacanth, sodium alginate or sodium carboxymethyl cellulose.

U.S. Pat. No. 5,256,402 discloses an aqueous abrasive toothpaste composition containing a peroxide compound which is stable with respect to active oxygen level and is effective for rapid whitening of teeth and stain removal which contains a mixture of at least 7% by weight water, 20 to 60% by weight calcium pyrophosphate, 1 to about 20% by weight of hydrogen or urea peroxide and about 0.5 to about 8.0% by weight of an alkali pyrophosphate salt. A drawback to the abrasive peroxide oral composition disclosed in U.S. Pat. No. 5,256,402 is that although the peroxide compound is stable, additional stability is required when the product is subjected to extended storage periods and abnormally high temperatures.

SUMMARY OF THE INVENTION

In accordance with the present invention, it has now been found that an aqueous abrasive dentifrice composition which contains a peroxide compound is physically and chemically stable and effects rapid whitening of teeth and stain removal is obtained using a composition containing an abrasive, a peroxide compound, a humectant containing a polyethylene glycol, a metal ion complexing agent, an antioxidant compound and a polyoxyethylene-polyoxypropylene block copolymer gelling agent, the pH of the dentifrice being buffered in the range of about 5.8 to about 7.2.

DESCRIPTION OF THE PREFERRED EMBODIMENTS

Abrasive compounds useful in the preparation of the whitening compositions of the present invention include dicalcium phosphate compounds. The term "dicalcium phosphate compound" as used herein includes within its meaning both dicalcium phosphate-dihydrate and anhydrous dicalcium phosphate or calcium pyrophosphate. A high beta phase calcium pyrophosphate is preferred as the abrasive compound for use in the present invention. The abrasive compound is incorporated in the whitening compositions of the present invention at a concentration of about 10 to 50% by weight and preferably about 20 to about 40% by weight.

The peroxide component of the composition of the invention is included in an amount sufficient to allow release of sufficient oxygen during brushing of teeth to effect whitening thereof. Typically, the peroxide compound can be employed in the composition of the present invention in amounts so that at least about 0.5% of the composition comprises a peroxide. Preferably, the peroxide comprises from about 0.5 to about 10% by weight of the composition. More preferably, the peroxide comprises from about 0.75 to about 5% by weight of the composition. Examples of suitable peroxide compounds used to prepare the compositions of the present invention include metal peroxides such as calcium peroxide, hydrogen peroxide and organic peroxides including urea peroxide, glyceryl peroxide, benzoyl peroxide and the like. A preferred peroxide compound is hydrogen peroxide.

The peroxide and abrasive compounds used to prepare the whitening composition of the present invention are dissolved or suspended in a vehicle comprised of water and a humectant such as a polyethylene glycol and glycerin. Water constitutes about 15 to about 40% by weight of the whitening composition of the present invention.

Illustrative of polyethylene glycols useful in the practice of the present invention include polyethylene glycols known by the trademark Carbowax which are nonionic polymers of ethylene oxide having the general formula: $HOCH_2(CH_2OCH_2)_nCH_2OH$ wherein n represents the average number of oxyethylene groups. The Carbowax polyethylene glycols are designated by a number such as 400, 600, 800, etc. which represents the average molecular weight. The molecular weight range of the polyethylene glycols used herein is about 200 to about 2000 and preferably about 600 hereinafter referred to as PEG 600.

The polyethylene glycol component included in the composition of the present invention constitutes about 10 to about 30% by weight of the whitening composition and preferably about 15 to about 20% by weight.

Glycerin may be included in the whitening composition of the present invention in the range from 0 to about 10% by weight of the whitening composition. Concentrations of glycerin substantially in excess of 10% by weight have been found to cause physical destabilization (liquefaction) of the composition and therefore such excess should be avoided.

When a combination of a polyethylene glycol and glycerin are used to prepare the whitening compositions of the present invention, it is critical to the physical (cosmetic) stability of the composition that the weight ratio of polyethylene glycol to glycerin be in excess of 1.0. As will hereinafter be demonstrated at weight ratios less than 1.0, phase separation of the components in the whitening composition occurs during storage at elevated temperatures.

Polyoxyethylene polyoxypropylene block copolymers gelling agents are included in the whitening compositions of the present invention in amounts from about 10% to about 25% by weight of the composition and preferably about 12 to about 20% by weight. Illustrative of polyoxyethylene polyoxypropylene block copolymers useful in the practice of the present invention are block copolymers having the formula $HO(C_2H_4O)_b(C_3H_6O)_a(C_2H_4O)_bH$ wherein a is an integer such that the hydrophobic base represented by $(C_3H_6O)$ has a molecular weight of about 2750 to 4000, b is an integer such that the hydrophilic portion represented by $(C_2H_4O)$ constitutes about 70–80% by weight of the copolymer. Block copolymers of this composition are available commercially under the trademark Pluronic F type.

Pluronic F127, which has a molecular weight of range of about 9000 to about 14000 and contains 70% of the hydrophilic polyoxyethylene moiety is preferred for use as a gelling agent in the practice of the present invention. When polyoxyethylene polypropylene block copolymers such as Pluronic F127 are used in the practice of the present invention, in order to obtain dentifrices characterized by the art as "ringing gels", it is necessary to use at least 15% by weight water in the manufacture of the dentifrice.

A combination of metal ion chelating agents and antioxidants (oxygen scavengers) are critical to the chemical stability of the whitening composition of the present invention. Examples of suitable metal ion chelating agents include alkali metal stannates such as sodium and potassium stannate, ethylenediaminetetracetic acid and its salts. Examples of antioxidants useful in the practice of the present invention include butylated hydroxy toluene (BHT), nordihydroguaiaretic acid, propyl gallate and trihydroxybutyrophenone. The metal ion complexing agents are incorporated in the compositions of the present invention at a concentration of about 0.01 to about 1% by weight and the antioxidant is incorporated at a concentration of about 0.05 to about 0.20% by weight and preferably about 0.02 to about 0.05% by weight.

In preparing the whitening compositions of the present invention, it is critical to buffer the pH of the composition in a range of about 5.8 to about 7.2. At a pH greater than about 7.2 there occurs a substantial diminution in the chemical stability of the composition. At pH's below about 5.8, the product although chemically stable has an unacceptable sour taste. The pH of the whitening composition may be adjusted with acidic inorganic and organic compounds having pH buffering capacity in the pH range of about 4.0 to about 9.0, such as phosphoric acid and its acid salts, $Na_2H_2PO_4$ and $Na_2H PO_4$, acetic acid and gluconic acid.

Pyrophosphate salts having anti-tartar efficacy such as dialkali or tetra-alkali metal pyrophosphate salts such as $Na_4P_2O_7$ (TSPP), $K_4P_2O_7$, $Na_2K_2P_2O_7$, $Na_2H_2P_2O_7$ (SAPP), and $K_2H_2P_2O_7$, may be included in the teeth whitening composition of the present invention at a concentration of about 0.5 to about 8.0% by weight and preferably about 1.5 to 3.5% by weight. In addition to their antitartar efficacy, pyrophosphate salts serve a dual function in the whitening compositions of the present invention as supplementary metal ion complexing agents. Further, certain pyrophosphate salts such as SAPP can be included to the composition of the present invention to adjust the pH of the composition to the desired pH range of about 5.8 to about 7.2.

Fluorine-providing salts having anti-caries efficacy may also be incorporated in the dentifrice of the present invention and are characterized by their ability to release fluoride ions in water, for example, sodium fluoride, potassium fluoride, a tin fluoride such as stannous fluoride, sodium fluorosilicate, ammonium fluorosilicate and sodium monofluorophosphate. It is preferable to employ a fluoride salt to release about 10–1500 ppm of fluoride ion.

A surfactant is also included in the whitening composition of the present invention and serves as a solubilizing, dispersing, emulsifying and wetting agent and is especially effective in solubilizing the flavor ingredient present. Surfactants which may be used in the practice of the present invention include cationic surfactants, anionic surfactants such as sodium laurylsulfate and sodium laurylsulfoacetate, ampholytic and amphoteric surfactants like cocoamidopropyl betaine.

The flavor ingredient constitutes about 0.5–5.0% by weight of the dentifrice composition of the present invention. Suitable flavoring constituents are flavoring oils, e.g., oils of spearmint, peppermint, wintergreen, menthol, cineole, limonene, menthone and menthyl acetate.

A sweetening material is preferably also employed as a complement to the flavoring material. Suitable sweetening agents are water soluble and include sodium saccharin, sodium cyclamate, xylitol, aspartame and the like, in concentrations of about 0.01 to 1.0% by weight. Sodium saccharin is preferred.

To prepare the whitening compositions of the present invention, water soluble salts such as sodium saccharin and sodium monoflurophosphate (NaMFP) are dissolved in an aqueous vehicle containing a humectant such as PEG 600 and glycerin. The vehicle is heated to a temperature of about 130°–170° C., followed by the addition of a polyoxyethylene-polyoxypropylene block copolymer gelling agent and the ingredients are mixed until a gel phase is formed. An abrasive compound such as calcium pyrophosphate is added to the gel and mixed to form a paste. The paste when formed is cooled to about 90°–130° F., preferably about 100° F. A metal ion chelating agent, antioxidant, buffering agent and peroxide compound are then added to the paste and the ingredients mixed to obtain an homogenous mixture. The flavor and surfactant, are then added to the mixture to obtain a finished tooth whitening paste of the present invention.

It has been determined that when pyrophosphate salts are used in the manufacture of the whitening compositions of the present invention, attempts to dissolve such salts in the aqueous vehicle at temperatures in excess of 130° F. should be avoided as such temperature conditions bring into solution levels of pyrophosphate salt in excess of the solubility capacity of the salt thereby creating a supersaturated condition with respect to the excess salt. During storage at lower, ambient temperatures, the excess pyrophosphate salt crystallizes out from the whitening composition matrix forming insoluble solid matter which is cosmetically unacceptable and may have the further disadvantage of promoting chemical instability.

It is therefore preferred in the practice of the present invention, that when pyrophosphate salts are to be included in the whitening formulation that during the manufacture of the whitening composition any pyrophosphate salt added to the composition is premixed in the humectant and the premixture added to the composition matrix at a temperature no higher than 100° F.

The following examples are further illustrative of the present invention, but it is understood that the invention is not limited thereto. All amounts and proportions referred to herein and in the appended claims are by weight unless otherwise indicated.

EXAMPLE I

A series of whitening peroxide toothpastes (Compositions A, B, C and D) was prepared. The ingredients of Compositions A-D are recorded in Table I below.

TABLE 1

COMPOSITIONS A–D

| Composition Ingredient | A | B | C | D |
|---|---|---|---|---|
| | PERCENT (%) BY WEIGHT | | | |
| PEG 600 | 17.42 | 17.42 | 17.42 | 17.42 |
| Glycerin | 7.42 | 7.42 | 7.42 | 7.42 |
| TSPP | 2.00 | 2.00 | 2.00 | 2.00 |
| Water | 26.09 | 25.84 | 25.59 | 25.34 |
| Na MFP | 0.76 | 0.76 | 0.76 | 0.76 |
| Saccharin | 0.50 | 0.50 | 0.50 | 0.50 |
| Pluronic F-127 | 15.00 | 15.00 | 15.00 | 15.00 |
| Calcium Pyrophosphate | 25.00 | 25.00 | 25.00 | 25.00 |
| Phosphoric Acid | — | 0.25 | 0.50 | 0.75 |
| Potassium Stannate | 0.45 | 0.45 | 0.45 | 0.45 |
| H2O2 (35%) | 3.43 | 3.43 | 3.43 | 3.43 |
| Flavor | 1.10 | 1.10 | 0.03 | 0.03 |
| BHT | 0.03 | 0.03 | 1.10 | 1.10 |
| SLS | 0.80 | 0.8 | 0.8 | 0.8 |
| pH | 7.02 | 6.70 | 6.55 | 6.22 |

The compositions were prepared by dispersing TSPP in a mixture of PEG 600 and glycerin and heating to 130° F. while stirring. Water was added to the mixture and the ingredients mixed for about 5 minutes Saccharin and sodium monofluorophosphate (Na MFP) were added and the resultant mixture stirred for 10 minutes, followed by the addition of Pluronic F127 and stirring at 130° F., for 20 minutes. The mixture was then deaerated for 5 minutes and calcium pyrophosphate was added and the resulting paste mixed for 15 minutes at high speed under vacuum. Potassium stannate premixed with $H_2O_2$ was added to the paste which was further mixed for 10 minutes under vacuum at high speed. BHT premixed with flavor oil was then added to the paste and mixed under vacuum for 5 minutes. Sodium lauryl sulfate (SLS) was then added under vacuum for 5 minutes at low speed. When necessary, phosphoric acid was added to adjust the pH of the composition to the desired level.

The $H_2O_2$ content of Compositions A–D was determined wherein the compositions were packed in separate plastic tubes, capped and stored at 105° F. for 12 weeks. Thereafter, the $H_2O_2$ content of Compositions A–D was again measured. The results are recorded in Table II below and show the effect of pH on the loss rate of $H_2O_2$ the for Compositions. The minimum $H_2O_2$ retained in the composition that is deemed acceptable for commercial use is 70%.

TABLE II

COMPOSITION CHEMICAL STABILITY

| Composition | pH (Initial) | % $H_2O_2$ (Initial) | % $H_2O_2$ After 12 wks @ 105° F. | % Retained |
|---|---|---|---|---|
| A | 7.02 | 1.220 | 0.866 | 71 |
| B | 6.70 | 1.215 | 0.916 | 75 |
| C | 6.55 | 1.220 | 0.947 | 78 |
| D | 6.22 | 1.219 | 1.002 | 82 |

The data recorded in Table II show that increasing the pH of the composition results in a decrease in $H_2O_2$ recovery. When the pH of the composition is greater than 7.2 the $H_2O_2$ recovery has found to be less than 70%.

EXAMPLE II

The procedure of Example I was repeated to prepare a whitening composition of the present invention (Composition E) which contained both a metal chelating agent (sodium stannate) and an antioxidant (BHT). The procedure was repeated to prepare Composition F to which only sodium stannate was added and Composition G in which both sodium stannate and BHT were not included in the composition. The ingredients of Compositions E–G are recorded in Table III below.

TABLE III

COMPOSITIONS E–G

| Composition Ingredients | E | F | G |
|---|---|---|---|
| | PERCENT (%) BY WEIGHT | | |
| PEG 600 | 17.00 | 17.00 | 17.00 |
| SAPP | 2.00 | 2.00 | 2.00 |
| Water | 28.96 | 29.09 | 28.67 |
| Na MFP | 0.76 | 0.76 | 0.76 |
| Saccharin | 0.50 | 0.50 | 0.50 |
| Pluronic F-127 | 15.00 | 15.00 | 15.00 |
| Calcium Pyrophosphate | 30.00 | 30.00 | 30.00 |
| Povidone USP* | 0.25 | 0.25 | 0.25 |
| Sodium Stannate | 0.10 | 0.10 | 0** |
| $H_2O_2$ (30%) | 3.60 | 3.60 | 3.60 |
| Flavor | 1.00 | 1.00 | 1.00 |
| BHT | 0.03 | — | — |
| SLS | 0.80 | 0.8 | 0.8 |
| pH | 5.9 | 5.9 | 5.9 |

*Polyvinyl pyrolidone
**Less than 1% ppm potassium stannate present in $H_2O_2$ used to prepare composition.

Compositions E–G were tested for chemical stability for 3 weeks at 120° F. following the procedure of Example I. The % $H_2O_2$ retained in Compositions E–F is recorded in Table IV below.

TABLE IV

CHEMICAL STABILITY

| Composition | % $H_2O_2$ (Initial) | % $H_2O_2$ After 3 wks @ 120° F. | % Retained |
|---|---|---|---|
| E | 1.080 | 1.026 | 95 |
| F | 1.080 | 0.910 | 84 |
| G | 1.080 | 0.872 | 81 |

The data recorded in Table IV show that a higher $H_2O_2$ retention is achieved when both sodium stannate and BHT are included in the peroxide whitening composition (Composition E) whereas the peroxide whitening composition exhibits a lower retention when BHT is absent from the composition (Composition F) or neither BHT or sodium stannate are added to the composition (Composition G).

EXAMPLE III

The procedure in Example I was used to prepare the whitening composition of the present invention which contained both a metal chelating agent (potassium stannate) (Composition H) and an antioxidant (BHT). For purposes of comparison, the procedure was repeated to prepare Composition I, which contained only BHT, but without the stannate ion being present. The ingredients of Composition H and Composition I are recorded in V below.

TABLE V

COMPOSITIONS H–I

| Composition Ingredients | H | I |
|---|---|---|
| | PERCENT (%) BY WEIGHT | |
| PEG 600 | 17.42 | 17.42 |
| Glycerin | 7.42 | 7.42 |
| TSPP | 2.00 | 2.00 |
| Water | 26.14 | 25.69 |
| MFP | 0.76 | 0.76 |
| Sacharin | 0.50 | 0.50 |
| Pluronic F127 | 15.00 | 15.00 |
| Calcium Pyrophosphate | 25.00 | 25.00 |
| Phosphoric Acid | 0.50 | 0.50 |
| Potassium Stanate (11% solution) | — | 0.45 |
| H2O2 (35%) | 3.43 | 3.43 |
| Flavor | 1.00 | 1.00 |
| BHT | 0.03 | 0.03 |
| SLS | 0.8 | 0.80 |
| pH | 6.50 | 6.50 |

Compositions H and I were tested for chemical stability for 1 week at 140° F. following the procedure of Example 1. The % $H_2O_2$ retained in of Compositions H and I is recorded in Table VI below.

TABLE VI

CHEMICAL STABILITY

| Composition | % $H_2O_2$ (Initial) | % $H_2O_2$ After 1 wk @ 140° F. | % Retained |
|---|---|---|---|
| H | 1.152 | 1.144 | 96 |
| I | 1.344 | 1.146 | 85 |

The data in Table VI indicate that the combination of potassium stannate and BHT is necessary to achieve maximum chemical stability.

EXAMPLE IV

The procedure of Example I was repeated to prepare a whitening composition of the present invention (Composition J) containing polyethylene glycol 600 and glycerin wherein the weight ratio of polyethylene glycol to glycerin was 2.4.

For purposes of comparison the procedure was repeated to prepare comparative Composition K with the exception that the polyethylene glycol/glycerin weight ratio was adjusted to be less than 1, namely 0.8. The ingredients of Composition J and comparative Composition K are recorded in Table VII below.

TABLE VII

COMPOSITIONS J–K

| Composition Ingredients | J | K |
|---|---|---|
| | PERCENT (%) BY WEIGHT | |
| PEG 600 | 17.42 | 12.00 |
| Glycerin | 7.42 | 15.00 |
| TSPP | 1.00 | 1.00 |
| SAPP | 1.00 | 1.00 |
| DI Water | 26.19 | 19.21 |
| MFP | 0.76 | 0.76 |
| Saccharin | 0.50 | 0.80 |
| Pluronic F-127 | 15.00 | 15.00 |
| Calcium Pyrophospate | 25.00 | 30.00 |

TABLE VII-continued

COMPOSITIONS J-K

| Composition Ingredients | J | K |
|---|---|---|
| | PERCENT (%) BY WEIGHT | |
| Potassium Stannate | 0.45 | — |
| Sodium Stannate | — | 0.1 |
| H2O2 (35%) | 3.43 | 3.20 |
| Flavor | 1.00 | 1.10 |
| BHT | 0.03 | 0.03 |
| SLS | 0.80 | 0.80 |
| pH | 6.50 | 6.55 |

The physical stability of Compositions J and K was determined by packing the compositions in individual plastic tubes, capping the tubes and storing the tubes for 8 weeks at 120° F.

Examination of the tube contents after the 8 week storage period indicated that no separation of ingredients had occurred in Composition J whereas composition K had separated into two discernible phases, one clear and the other white opaque.

EXAMPLE VI

A whitening Composition L containing the ingredients of Composition B of Example I was prepared by dissolving sodium saccharin and NaMFP in a solution of PEG 600 and water. The solution was heated to 160° F. followed by the addition of Pluronic F-127. The mixing was continued until a gel phase was formed. Calcium pyrophosphate was added to the gel and the resulting dispersion was cooled to 100° F. Potassium stannate was added to the cooled dispersion followed by the addition of phosphoric acid and TSPP and the resulting system was mixed for about 10 minutes followed by the addition of hydrogen peroxide, flavor and SLS. The pH of the finished product was 6.8.

The procedure of Example VI was repeated to prepare a whitening Composition M with the exception that TSPP was added initially to a solution of PEG 600, water and glycerin containing saccharan and NaMFP which was heated to 160° F. before the addition of the other ingredients of the composition.

The chemical stability of Compositions L and M was determined by initially analyzing the compositions for hydrogen peroxide and then storing the composition for a 6.5 week period at 120° F. and then again analyzing the composition for $H_2O_2$ content.

The results of these analyses are summarized in Table VII below.

TABLE VII

COMPOSITION CHEMICAL STABILITY

| Composition | % $H_2O_2$ (Initial) | % $H_2O_2$ After 6.5 Wks @ 120° F. | % Retained |
|---|---|---|---|
| L | 1.265 | 0.899 | 71.1 |
| M | 1.366 | 0.687 | 49.8 |

The data recorded in Table VII indicate that the chemical stability of Composition L is acceptable when in the process of manufacture TSPP is added to the composition at a temperature of 100° F. rather than at elevated temperatures, i.e., 160° F., as was the case for Composition M which had unacceptable chemical stability, i.e., an $H_2O_2$ recovery of 49.8%.

After the 6.5 week test period, samples of Composition L when examined were found to be smooth to the touch with no preceptible particles whereas numerous particles could be seen and felt in Composition M.

What is claimed is:

1. A method for preparing an aqueous tooth whitening composition containing an abrasive and a peroxide compound which is chemically and physically stable and effects whitening and stain removal from teeth which comprises admixing water, a peroxide compound, a humectant containing polyethylene glycol, and a polyoxyethylene polyoxypropylene block copolymer gelling agent, heating the admixture to a temperature of about 130° to 170° C. until a gel phase is formed, adding a calcium phosphate abrasive compound to the gel to form a paste, cooling the paste to about 90° F. to 130° F. and then adding 0.01 to about 1% by weight of a metal ion chelating agent, about 0.05 to about 0.20% by weight of an antioxidant, and an alkali metal pyrophosphate buffering agent effective to buffer the pH of the composition in the range of about 5.8 to about 7.2 and then heating the admixture to a temperature between about 90° to about 170° F., the buffering agent being added to the composition ingredients at a temperature no higher than 100° F.

2. The method of claim 1 wherein the peroxide is hydrogen peroxide.

3. The method of claim 1 wherein the peroxide compound is present in the admixture at a concentration of about 0.5 to about 10% by weight of the admixture.

4. The method of claim 1 wherein the abrasive compound is calcium pyrophosphate.

5. The method of claim 1 wherein the abrasive compound is present in the admixture at a concentration of about 10 to about 50% by weight of the admixture.

6. The method of claim 1 wherein the humectant is a combination of polyethylene glycol and glycerin.

7. The method of claim 6 wherein the weight ratio of polyethylene glycol to glycerin is greater than 1.0.

8. The method of claim 1 wherein the polyethylene glycol has an average molecular weight of about 600.

9. The method of claim 1 wherein the metal ion chelating agent is potassium stannate.

10. The method of claim 1 wherein the antioxidant is BHT.

11. The method of claim 1 wherein the polyoxyethylene polyoxypropylene block copolymer gelling agent has molecular weight of about 9000 to about 14000.

12. The method of claim 1 wherein the composition is buffered to a pH between 6.2 and 7.0.

* * * * *